US010507283B2

(12) United States Patent
Lee et al.

(10) Patent No.: US 10,507,283 B2
(45) Date of Patent: Dec. 17, 2019

(54) MEDICAL PUMP SYSTEM FOR IMPROVED PAIN MANAGEMENT

(71) Applicant: Zyno Medical, LLC., Natick, MA (US)

(72) Inventors: Chaoyoung Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 496 days.

(21) Appl. No.: 14/721,670

(22) Filed: May 26, 2015

(65) Prior Publication Data
US 2016/0346468 A1 Dec. 1, 2016

(51) Int. Cl.
*A61M 5/172* (2006.01)
*A61M 5/14* (2006.01)

(52) U.S. Cl.
CPC ..... *A61M 5/172* (2013.01); *A61M 2005/1405* (2013.01); *A61M 2205/276* (2013.01); *A61M 2205/3379* (2013.01); *A61M 2205/3569* (2013.01); *A61M 2205/3584* (2013.01); *A61M 2205/52* (2013.01)

(58) Field of Classification Search
CPC .......... A61M 5/172; A61M 2005/1405; A61M 2205/276; A61M 2205/3379; A61M 2205/3569; A61M 2205/3584; A61M 2205/52
See application file for complete search history.

(56) References Cited

U.S. PATENT DOCUMENTS

| | | | | |
|---|---|---|---|---|
| 6,231,560 | B1* | 5/2001 | Bui | A61M 5/1723 604/500 |
| 7,559,926 | B1* | 7/2009 | Blischak | A61M 5/14276 604/890.1 |
| 7,806,852 | B1* | 10/2010 | Jurson | A61B 5/1172 604/151 |
| 2003/0051737 | A1* | 3/2003 | Hickle | A61M 5/1723 128/898 |
| 2013/0012880 | A1* | 1/2013 | Blomquist | A61M 5/142 604/151 |
| 2013/0144206 | A1 | 6/2013 | Lee et al. | |
| 2014/0194817 | A1 | 7/2014 | Lee et al. | |
| 2014/0276549 | A1* | 9/2014 | Osorio | A61M 5/1723 604/503 |
| 2016/0074575 | A1* | 3/2016 | Hyun | A61M 5/14216 604/152 |

* cited by examiner

*Primary Examiner* — Lauren P Farrar
(74) *Attorney, Agent, or Firm* — Boyle Fredrickson S.C.

(57) ABSTRACT

A pump system for pain management may receive input related to a patient's real-time pain to provide automatic adjustments of pain medication bolus delivery based on deduced patient pain. The pump may also collect pain management information during the delivery of pain medication to provide data for improved pain management protocols.

17 Claims, 5 Drawing Sheets

MEDICAL PUMP SYSTEM FOR IMPROVED PAIN MANAGEMENT

BACKGROUND OF THE INVENTION

The present invention relates to medical pumps for the deliver of pain medication and in particular to a medical pump system providing improved pain management.

The management of pain, for example, associated with postsurgical recovery, is increasingly recognized as an important part of the healthcare process. Nevertheless, because pain is highly subjective and unique to an individual, assessing and responding to patient pain can be difficult. In addition, medications for the management of pain can have serious drawbacks including toxicity and the promotion of dependency on the medication. For these reasons, the management of pain requires that both of the problems of too much or too little pain medication be addressed.

It is generally understood to provide surveys to the patient to better understand the level of pain that the patient is experiencing. These surveys may be administered periodically by hospital personnel, in addition, on-demand pain medication systems, for example, that deliver a bolus of pain medication when requested by the patient, are known for providing the patient with greater control over pain relief. The decision about pain medication, however, cannot be left completely to the patient who will typically be underinformed with respect to the risks of the pain medication.

Although pain management is important to proper delivery of healthcare, understanding and managing the problem for each patient can be difficult and time-consuming for the healthcare organization.

SUMMARY OF THE INVENTION

The present invention provides a medical pump system that simplifies the management of pain in a healthcare environment by collecting, recording, and presenting to the healthcare professional more comprehensive pain management data including, for example, data about patient-professed pain levels, bolus demand by the patient and actual medication delivery rates. In addition, the medical pump may provide for a heuristic pain medication rate control to implement, according to settings by the healthcare professional, a more sophisticated real-time pain management solution that gives the patient more control over their treatment.

Specifically, the invention provides a pump system for managing pain medication and having a pump for the delivery of a pain medication to a patient from a reservoir through a line to a patient and an input device for receiving input from the patient related, to real time pain during delivery of the pain medication. An electronic computer in the pump communicates with the pump and the input, device to: (a) provide a schedule of pain medication delivery having a delivery rate; (b) control the pump to provide the delivery rate of pain medication through the line to the patient; (c) receive a bolus command from the patient and responding by controlling the pump to deliver a discrete bolus of pain medication through the line beyond the delivery rate, the bolus having a bolus volume at a frequency not greater than a bolus lockout time after any previous delivery of a discrete bolus to the patient; and (d) respond to the input from the patient related to real time pain, through the input device, to adjust at least one of the bolus volume, the bolus lockout time, and the delivery rate.

It is thus a feature of at least one embodiment of the invention to provide better pain management by offloading more sophisticated pain management features into the pump controlling the pain medication in real-time. It is another feature of at least one embodiment of the invention to anticipate patient pain (for example by adjusting ongoing dosages) rather than only react to patient pain after-the-fact as occurs with simple bolus delivery systems.

The bolus command may be used as the input from the patient that indicates the patient's real time pain.

It is thus a feature of at least one embodiment of the invention to make use of existing hardware with more sophisticated software that can deduce patient pain level from bolus requests.

Alternatively or in addition, the input from, the patient related to real-time pain may be a response to a real-time survey soliciting information about pain from the patient.

It is thus a feature of at least one embodiment of the invention to provide direct solicitation of pain information from the patient without the need for the patient to request a bolus of pain medication thereby providing more direct information about pain and a better understanding of pain in patients who nevertheless resist using the bolus feature.

The real-time survey may provide the patient with a scale of pain levels including descriptions of pain at each level to return a pain quantity.

It is thus a feature of at least one embodiment of the invention to permit the pump to use a pain metric that can be consistent with other surveys adopted by the healthcare institution.

Step (d) may respond to a trending of patient input related to real-time pain over a period of time.

It is thus a feature of at least one embodiment of the invention to anticipate patient pain trends to better optimize the delivery of pain medication without "under shooting" and "overshooting".

The pump may include a wireless transceiver and the schedule may be received wirelessly from a remote device.

It is thus a feature of at least one embodiment of the invention to simplify the delivery of more sophisticated pain management protocols to the pump making the ability to use more sophisticated pain management protocols practical, in the real healthcare environment.

The patient input device may be a wireless portable device such as a tablet or smart phone.

It is thus a feature of at least one embodiment of the invention to make use of prevalent commercial technology to improve the communication from the patient related to pain and pain management.

The pump may record at least one of an input from the patient related to real-time pain and bolus commands over time to provide a history of patient pain over a time of delivery of the pain medication.

It is thus a feature of at least one embodiment of the invention to capture historical information about the change in the patient's experience with pain during the treatment to permit better pain management and the development of more sophisticated pain management protocols.

When the proxy for patient pain is received bolus commands and the pump may record whether the pump response to the bolus command or whether the bolus command is denied as being within the bolus lockout time.

It is thus a feature of at least one embodiment of the invention to provide a more sophisticated understanding of patient pain by capturing both delivered boluses and requests for boluses that are not delivered.

This history of patient pain may be communicated wirelessly to a remote electronic medical record.

It is thus a feature of at least one embodiment of the invention to facilitate the capture of a rich data set related to pain management for the development of protocols and for the treatment ala given patient.

The pump may further record an indication of pain medication delivery over time to provide a history of pain medication delivery over the time of delivery of the pain medication.

It is thus a feature of at least one embodiment of the invention to provide data that allows comparison of pain medication delivery and pain perceived by the patient for a better understanding of bow to treat patient pain.

The real-time adjustment of pain medication dosage facilitated by the pump may both increase and decrees that dosage for example through adjustment of at least one of the bolus volume, the bolus lockout time, and the delivery rate.

It is thus a feature of at least one embodiment of the invention to provide improvement in pain management that also serves to reduce unnecessary pain medication.

These particular features and advantages may apply to only some embodiments failing within the claims and thus do not define the scope of the invention.

DETAILED DESCRIPTION OF THE PREFERRED EMBODIMENT

Figure 1:
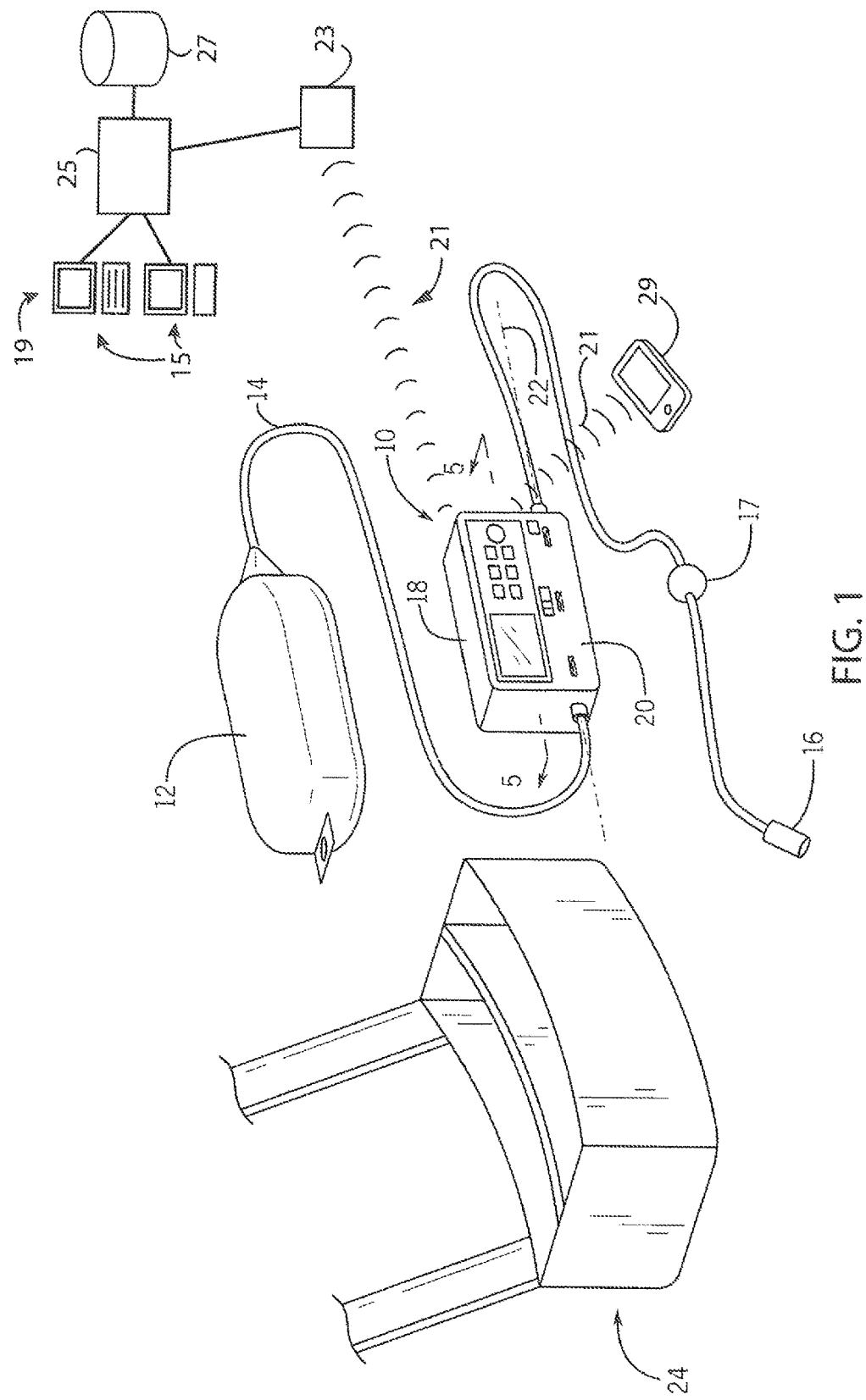
FIG. 1 is a simplified perspective view of the pain medication pump assembly as provided to a patient.

Referring now to FIG. 1, an ambulatory pump 10 for pain management may operate in eon unction with a medicament brig 12 holding pain medication and communicating with an IV line 14. The medicament bag 12 may be, for example, a flexible plastic bag of the type used to hold IV solutions, and the IV line 14 may provide a flexible tube allowing the flow of medicament from the medicament bag 12, and a patient connector 16 may communicate with the patient through a needle or port or the like. The IV line 14 may include a bubble filter 17 for removing included air bubbles, limiting the need for air bubble sensing.

The ambulatory pump 10 in this example may provide a two-part housing having an upper electronics portion 18 that may attach to a lower clamp portion 20 to receive the IV line 14 therebetween along a longitudinal axis 22 being generally the longest dimension of the housing of the ambulatory pump 10. As so received, the ambulatory pump 10 may pump liquid through the IV line 14 by peristaltic action.

In one embodiment, the ambulatory pump 10 is constructed to weigh less than a half pound and preferably to be sized less than 1.5" by 2" by 5" so as to be easily carried by the patient, for example, in a pouch 24 also sized to receive the medicament bag 12. The invention also contemplates its applicability to larger stationary pumps used in a hospital or the like.

As discussed in more detail below, the ambulatory pump ID may communicate with a remote computer system 19 for the exchange of data and programming information (e.g. protocol information) therebetween. This communication may be wirelessly through a Bluetooth or cellular connection 21 or may make use of standard electrical connectors (not shown). Generally, the communication may be via transceiver 23 (for example, a wireless access point) in turn communicating with a central server 25 operating to access a patient database 27, the latter, for example, being part of an electronic medical record (EMR). For this purpose, the server 25 may communicate with one or more terminal systems 15 so that data may be entered into and read from the electronic medical record. As is understood in the art, the central server 25 will hold one or more computer processors together with memory for storing a program for execution by the processors.

The ambulatory pump 10 may also communicate with a patient device 29 such as a smart phone, laptop, or tablet or similar device or the like through a local wireless connection Bluetooth) or by means of a cellular network or the like. This communication may use a specialized application program or may use conventional e-mail or text messaging channels or may provide for a web-based application accessible through any browser. As will be discussed below, patient input may be obtained alternatively or in addition by using the pump keypad pushbuttons 30 or display 28.

Figure 2:
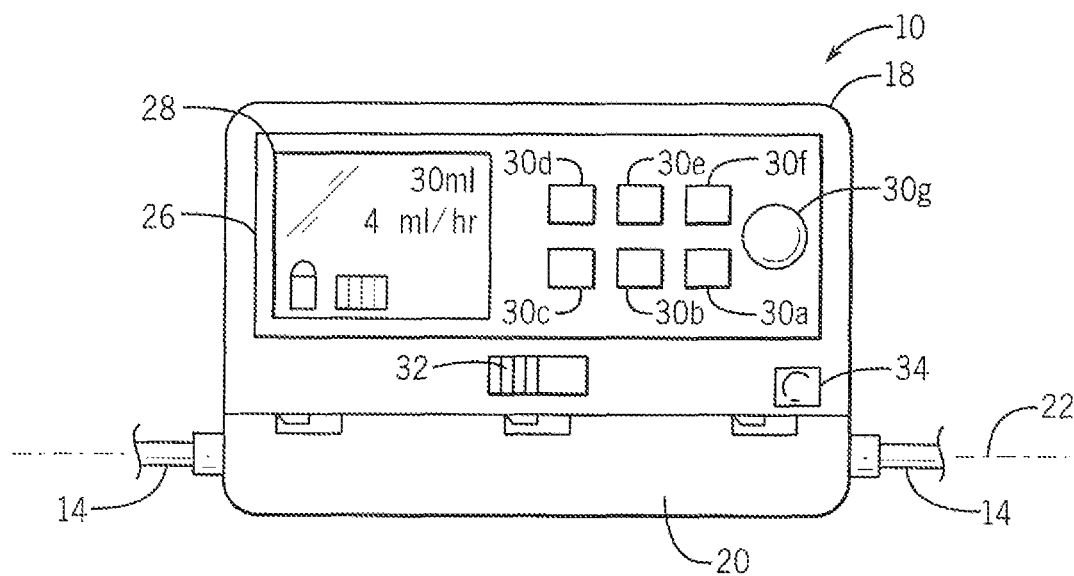
FIG. 2 is a front elevational view of the pump showing inter-assembly of an upper active portion and lower clamp portion of the housing as separated by operation of dual re lease elements and showing a user interface comprising a display and manually operated buttons.

Referring now to FIG. 2, the housing of the upper active portion may present on its front surface a user interface 26 comprising, for example, a liquid crystal type display 28 for displaying symbols and alphanumeric characters under computer control. The user interface 26 also provides multiple membrane switch pushbuttons 30 that may be activated by a user or a healthcare professional, the latter requiring, entry of as password lock, for example, through sequencing of keypresses.

Generally, the user accessible pushbuttons include a limited number of controls including, in one embodiment, run and stop pushbuttons 30a and 30b, respectively, that will stop and start operation of the pump 10 as will be described below. Pushbutton 30f allows the unit to be turned on and off to conserve power. A bolus pushbutton 30 allows short operation of the pump 10 to deliver medicament in fixed, patient controlled bolus quantities.

As noted above, a health-care professional may also use the front panel to enter data, for example, through a rate pushbutton 30c that allows setting of the maximum pumping rate of the ambulatory pump 10 in milliliters per hour. This entry may select one or more preset values from a menu by cycling through menu standard rates with each push. The pushbuttons also include a "volume to be infused" pushbutton 30d allowing user control of the maximum volume to be infused during a treatment protocol, also by cycling through standard settings with each push, as well as basal rate pushbutton 30e allowing setting of a basal pumping rate of the pain medication using a similar mechanism. As will be discussed below, other settings may be made by the healthcare professional using wireless communications and may include as set of timing parameters to be discussed below as well, as more general rules allowing the pump 10 to better manage a patient's pain.

A lower edge of the upper electronics portion 18 provides for a clamp release slide 32 as will be described below and safety lock 34 that must be simultaneously activated to remove the lower clamp portion 20.

Figure 3:
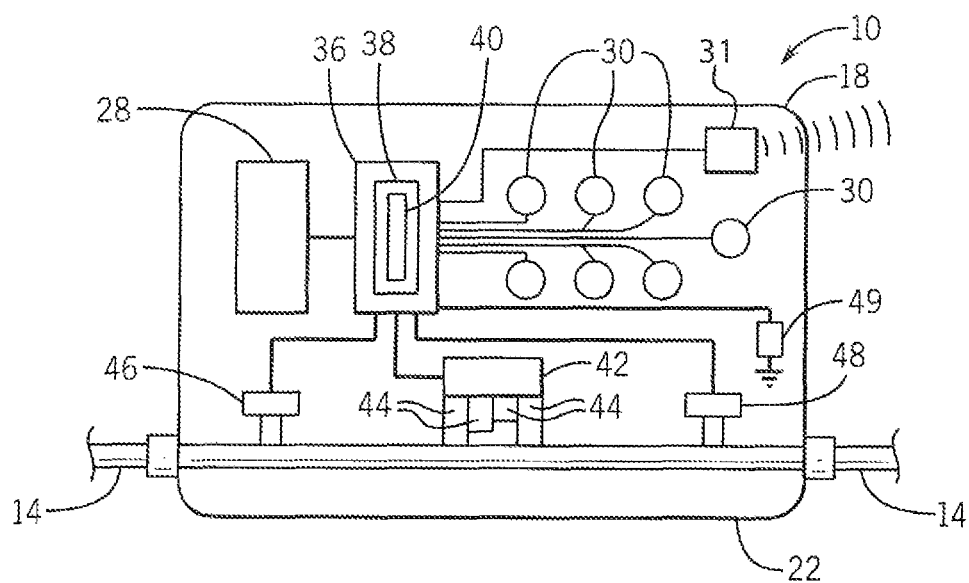
FIG. 3 is a simplified block diagram of the electronics of the pump of FIGS. 1 and 2 as controlled by an internal electronic computer executing a stored program.

Referring now to FIG. 3, the ambulatory pump 10 may include a microcontroller 36 being an electronic computer having a self-contained nonvolatile memory 38 holding an operating program 40 and necessary storage variables as will be described below. The nonvolatile memory may comprise, for example, flash memory and/or read-only memory, or other similar nonvolatile memory as context requires, which may store data values to be retained even in the absence of electrical power.

The microcontroller 36 also provides various input and output lines communicating, for example, with the display 28 for providing display information thereon and various pushbuttons 30 for receiving data related to their activation by a user. In addition, the microcontroller 36 may provide control lines to the pump assembly 42 having, for example, an internal DC electric motor (not shown) operating through a gear system to activate peristaltic plunger elements 44 that may press against the contained IV line 14 to push fluid therethrough. As is understood in the art, generally the peristaltic plunger elements 44 extend in an undulating serpentine fashion to compress and release the tubing thereby moving fluid therethrough.

The microcontroller 36 may also communicate electrically with various sensors. For example, upstream and downstream pressure sensors 46 and 48 which can be used to ensure proper operation of the pump by detecting abnormal pressures and provide alarms as described below. Generally each of the pressure sensors 46 and 48 may provide a spring-loaded plunger that presses into the outer wall of the IV line 14 to sense pressure. This through-wall measurement avoids the need for separate connections to the fluid-contacting pressure sensor and the problems of sterilization of a fluid-contacting pressure sensor. In such a through-tubing sensing system, the spring-loaded plunger deforms a portion of a wall of the line 14 as held against a backstop. Under a known spring biasing force, the amount of deflection of the wall may be measured to deduce internal pressure. Generally, lower pressures of the contained medicament will allow greater deflection of the wall of the IV line 14 and higher pressures of contained medicament will allow less deflection of the wall of the IV line 14. The system may be calibrated for a particular material of the IV line 14.

All electrical components in the upper electronics portion 18 maybe supplied with power by a contained storage battery 49 that may provide its power directly or through standard power processing circuits such as regulators and the like. In addition, the microcontroller 36 may communicate with a wireless transceiver 31 for communication with the transceiver 23, for example, by any known wireless or wired transmission protocol. The microcontroller 36 may also communicate with one or multiple patient devices 29 and with other medical devices including but not limited to other pumps, patient monitors for heartbeat, respiration, etc. The pump hardware and software may incorporate features from U.S. Patent 2014/0194817 "Medical Pump with Operator-Authorization Awareness and U.S. Patent 2013/0144206 Medical Device with Contextual Awareness, both assigned to the assignee of the present invention and hereby incorporated, by reference.

Figure 4:
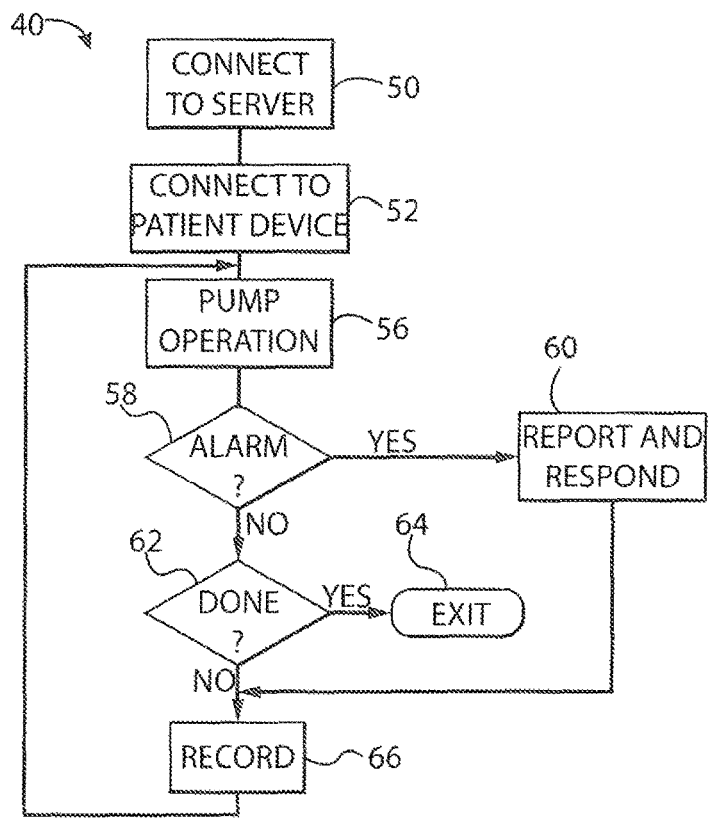
FIG. 4 is a simplified flowchart of the principal steps executed by the pump of FIG. 1 in providing, more comprehensive pain management solution.

Referring now to FIG. 4, the pump 10 may be commissioned as indicated by process block 50 of program 40 by establishing a connection to the server 25 or patient device 29 to receive programming related to the pumping rate of the pain medication as a function of time, identification of the pain medication, identification of the patient, a time window for use of the pump 10, and rules related to the patient adjustment of the basal rate including, for example, various time values which describe how frequently the patient may elect a bolus of drug delivery and other parameters used for heuristic delivery of pain medication as will be described below. These parameters may be set individually by a healthcare professional but preferably is in the form of a protocol for particular medical situation, for example, which may be selected to provide for the setting of a many of parameters and operational characteristics of the pump 10 to free the healthcare professional from the complexity of this programming. As will be discussed below, these protocols may be refined and developed with information collected by the pump 10

At process block 52, the pump may optionally connect with the patient device 29 which may serve to provide control to the pump (for example, providing a virtual bolus button 30g) as well as the ability to take periodic surveys of pain, which data may be collected by the pump 10. The surveys, for example, may be conducted from an application on a smart phone serving as the patient device 29 or via, text or e-mail communications and may, for example, describe a scale from 1 to 5 with descriptions of different degrees of pain and possibly a caricature of a face of an individual in those pain degrees. In this way, the patient can respond with a quantitative indication of pain, for example, by text entry (including numerics). The surveys could also include information about other pain management activities, such as taking oral pain medicine or other pain treatment techniques, including the type of medication or procedure, the time it was taken and the dosage or the like. This information may be used as part of a protocol to adjust the delivery of pain medication as described below and/or may be recorded and used for the development of such protocols. Otherwise, the pump 10 may operate to connect via the front panel controls described above. This connection, as of the discussed below, allows the collection of real time pain survey data from the patient but may also be used to deliver instructional information to the patient, for example, on setting up the pump or removing the catheter and returning the pump after completion.

The pump 10 may then enter into a loop in which pain medication is delivered according to a pre-stored protocol as will be discussed below. At process block 56 pumping may begin as moderated by patient input including pressing of the start button 30a and the bolus button 30g according to rules downloaded from the server 25 or otherwise entered. In addition at process block 56, the patient input may be solicited to complete pain surveys from the patient device 29.

Certain conditions as will be described may be detected as alarm conditions as indicated by process block 58 causing the pump 10 to report and respond to those alarm conditions 60, for example, by shutting down operation of the pump 10 in some cases, providing an audible alarm locally and/or reporting the alarm conditions in real time, for example, using the wireless transceiver 31.

If there is no alarm at decision block 62, completion of the pump operation is checked, for example, against the total infused volume of pain, medication to be delivered, and if the pumping is complete, the program proceeds to an end point 64 at which pumping stops. Otherwise, if the indicated drug volume has not been delivered, at process block 66 data related to the recent loop is recorded for storage in the pump 10 and transmission either in real time or subsequently to the server 25 as will be discussed below.

Note that generally, completion of the pump operation may be defined more broadly than a ceasing of the pumping of medication and the pump 10 may continue to operate after completion of the delivery of medication to continue to record data, for example, about the perception of pain by the patient that may have value for future treatment.

The data collected by the pump 10 may include but is not limited to: alarm conditions, pain medication delivery rates, time and number of bolus button presses, and responses by the patient to surveys of about pain.

Figure 5:
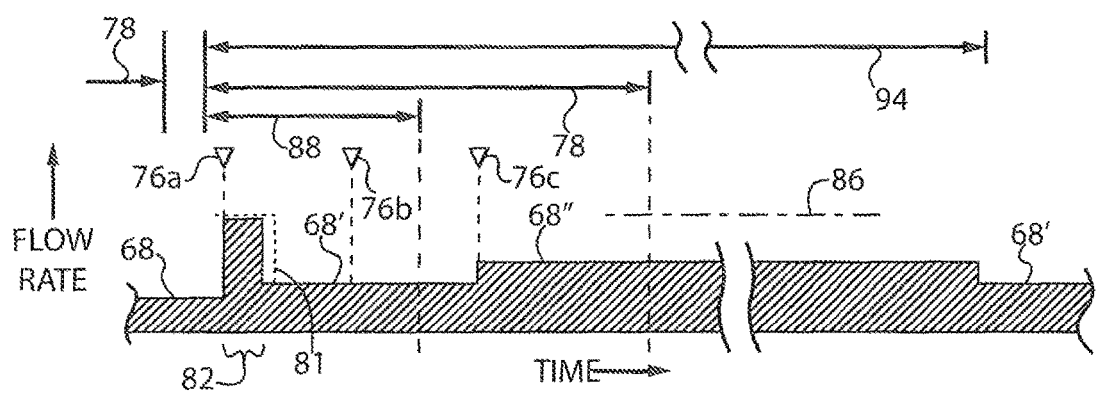
FIG. 5 is a diagram of pain medication delivery rate over time showing heuristic adjustment of a basal delivery rate, bolus lockout time or volume based on patient bolts demand.
Figure 6:
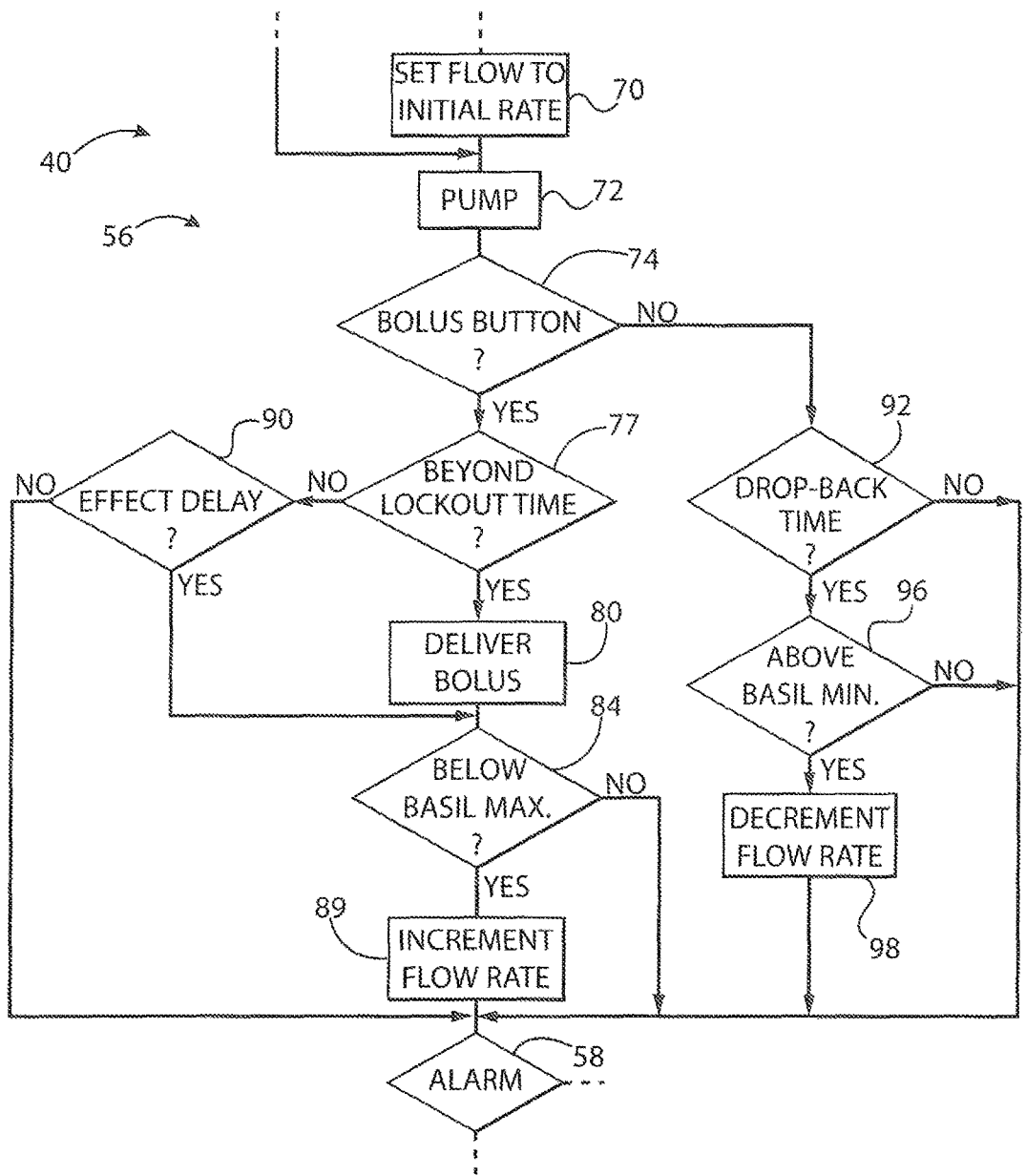
FIG. 6 is a flowchart of a portion of the program of FIG. 4 implemented by the pump of FIG. 1 in implementing a heuristic adjustment of medication delivery rate.

Referring now to FIGS. 5 and 6, the pumping operation of process block 56 may begin by setting the pump flow rate to a preprogrammed basal rate 68 being a flow rate according to process block 70. This process block 70 is only performed at the start of each pumping session and provides the healthcare professional's best judgment about the average amount of pain medication to be delivered based on the drug type and the condition of the patient. This number may be refined by data collected by the pump 10 as will be described below.

The pump 10 may then be energized per process block 72 to provide for the currently set basal flow rate. At decision block 74, bolus-pressing event 76a ma be detected in the program upon a pressing of bolus button 30g. In this case, at decision block 77, the pump 10 determines whether this bolus-pressing event 76a has occurred beyond a lockout time 78 after the previously detected bolus-pressing event 76 (not shown). This lockout time 78 may be set by the healthcare professional as discussed above and will generally be refined based on data collected by the pump 10. The lockout time 78 prevents the pump from delivering a bolus too frequently based, for example, on a balancing between drug toxicity and adverse effects, alleviation of pain, and the likely physiological delay in the patient's responding to a previous drug bolus.

If the current bolus-pressing event 76a is at the lockout time 78 of a previous bolus-pressing event 76, then at process block 80, a bolus is delivered causing the pump to provide a brief uptick in flowrate to a bolus rate over bolus delivery time 82.

At decision block 84, the basal rate 68 is checked to see if it is less than the maximum basal rate 86 and if so the basal rate 68 is incremented as indicated by process block 89 to new basal rate 68. This adjustment attempts to anticipate the patient's need for additional pain medication in the future before the patient pain is such as to require another pressing, of the bolus button 30g. Note that generally the basal rate 68 may include automatically delivered boluses and accordingly the basal rate 68 should be understood generally to include the possibility of one or both of a slowly changing, and quickly changing component that is automatically delivered.

The program 40 then proceeds to process block 58, as discussed above to check for alarm conditions, for example, related to drug delivery problems or pain conditions that may need to be reported to the healthcare professional, for example, a perceived pain level above a predetermined amount provided by the healthcare professional.

At decision block 74, a subsequent bolus-pressing event 76b may be received within the lockout time 78 after bolus-pressing event 76a and hence does not result in the delivery of a bolus per process block 80 but causes a branching at decision block 77 to decision block 90. At decision block 90, the timing of the bolas-pressing event 76b is compared against an effect lag time 88. The effect lag time 88 is a time before which it is unlikely that the effect of the previous bolus would have been fully felt by the patient. In this example, the bolus-pressing event 76b is before expiration of the effect lag time 88 and accordingly there is no incrementing of the basal rate per process block 89.

For subsequent bolus-pressing event 76c, occurring after the effect lag time 88 but before the lockout time 78 has occurred, at decision block 90, the program proceeds to decision block 84 as has been discussed and then to process block 89 where the basal rate may be adjusted upward to basal rate 68 yet without the delivery of a bolus. In this way, the patient is given additional control over the delivery of pain medications beyond simply the delivery of a bolus.

When, at decision block 74, no bolus-pressing event 76 is detected, the program 40 proceeds to process block 92 to see if at time elapsed since the last bolus-pressing event 76 exceeds a dropback time 94, if so, and if at decision block 96 the current basal rate is above the initial basal rate 68 set at process block 70, then at process block 98 the basal rate 68" may be decremented to basal rate 68'. In this way, the basal rate may be slowly decreased if there is no indication that the pain to the patient is excessive.

The operation of the program 40 and in particular of process block 56 will generally be defined by a protocol received during process block 50 of FIG. 4.

The amount of incrementing of the basal rate is a value that may be set by the healthcare professional during the commissioning process of process block 50 of FIG. 4 as well as the time periods for the dropback time 94, the bolus lockout time 78, and the effect lag time 88. In addition, these factors may be adjusted by the results of patient surveys conducted during this time to the patient device 29 with the patient or by trends in reported pain and delivered medicine.

While the above description describes adjustment of the basal rate, it will be appreciated that the same technique may be used to provide adjustment of bolos rate, bolus volume, bolus lockout time, effect lag time, and dropback time to provide analogous adjustment of the pain medication delivery in real time based on derived patient pain from patient input. So for example, instead of raising the basal rate, the bolus rate may be affected by controlling the bolus lockout time 78 or the bolus volume (being the area under the curve shown in FIG. 5 during bolus delivery time 82 either in excess of the basal rate 68 or in excess of zero flow rate) may be increased to similar effect. The bolus volume may control either of the flow rate during the bolus delivery time or the bolus delivery time 82 as shown by boundary 81.

Figure 7:
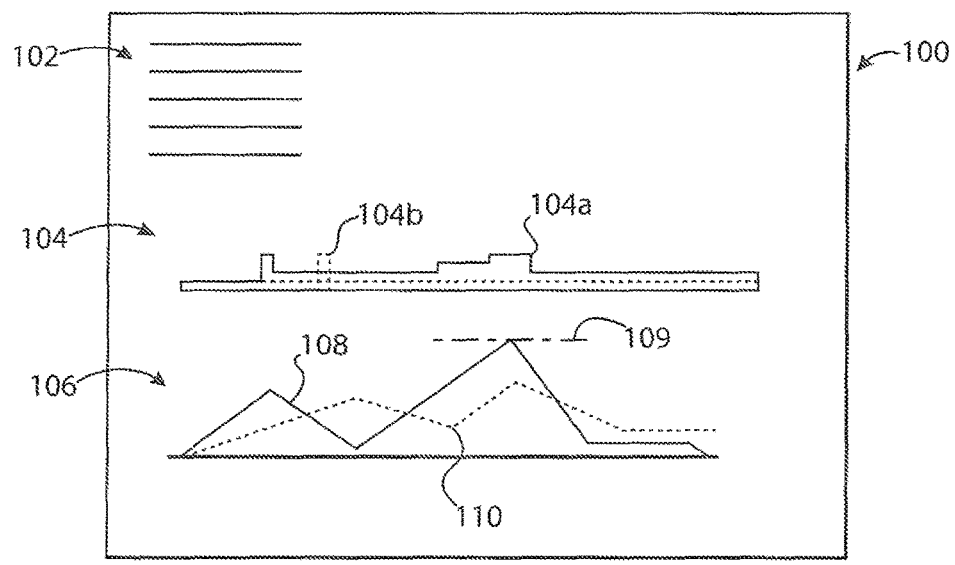
FIG. 7 is a graphic representation of example data collected on pain management by the pump for presentation to a healthcare professional.

Referring now to FIGS. 1 and 7, it will be understood that the present invention collects significant data that can assist the healthcare professional in managing patient pain. In this regard, data collected at process block 66 may be presented to the physician in the form of one or more reports 100. Generally, each report 100 will provide patient and treatment data 102 including the patient name, treatment date, medication type, and a link to other medical records related to the patient, in the EMR. The report 100 may provide a plot 104 of pain medication including plot line 104a showing the current or most recent basal delivery rate shown generally in FIG. 5 for the patient and any other pain medications such as oral pain medication shown by plot line 104b obtained from patient surveys allowing the healthcare professional to gain a better understand actual delivery of medication to the patient and to assist in the development of protocols to control the pump 10 in the future.

A second plot 106 may provide for insight into the patient's perception of pain including a first plot line 108 showing patient perceived pain, for example, derived from either a combination of pain surveys answered by the patient or bolus button pressing. For example, these different sources may be averaged after appropriate weighting. This data may be subject to a smoothing filter commensurate with the physiological perception of pain such as may be derived from empirical data collected by the present pump 10 for many patients. This is smoothing, filter also accommodates the episodic nature of the perceived pain data. The first plot line 108 may also be compared to a second plot line 110 showing the delivery of pain medication (also smoothed to represent the physiological effect of the medication) derived from plot 104. The physiological effect of medication may be refined by data collected by the present pump 10 and incorporated into the protocols implemented by the pump 10. The gap between lines 108 and 110 may be analyzed to develop improved rules for the delivery of the pain medication using the pump 10 which may be downloaded into the pump to refine the process described with respect to FIG. 6. This gap between lines 108 and 110 may also be used to provide dynamic adjustment of the pump in real time, for example, increasing drug delivery in response to the size of the gap. This increase may consider not only the gap size but its trending and thus may make use of the general control framework of proportional/integral/derivative (PID) control with these parameters being determined empirically impart from data collected by the pump 10 for many patients. Generally data of this type may be collected for different procedures for different drug medications to develop a schedule that may anticipate patient pain to better address the pain cycle after a particular medical procedure, in addition the absolute perceived pain level of plot line 108 may be compared to a maximum pain value 109 that triggers an alarm to a healthcare professional. The overall data for a pain delivery session may be abstracted to a pain management score, for example, being based on plot line 108, its peak values, or the area beneath the line.

Generally the data collected by the pump 10 may be used to prepare standard protocols that may be used to guide the delivery of pain medication in the future. The standard protocols may consider:
1. Location of the anesthesia,
2. Drug used, toxicity of the drug,
3. Total dose of the drug being applied within a time interval,
4. Patient request of bolus within a time interval,
5. Number of denied bolus request, and
6. Patient input pain score when pump denies a bolus request.

These protocols may provide functions controlling the changing of, time periods for the dropback time 94, the bolus lockout time 78, and/or the effect lag time 88 in response to any of the trending of pain values, the location of the anesthesia, the type of surgical procedure, and/or the age or other demographic variables of the patient. The protocols may also include initial values of the dropback time 94, the bolus lockout time 78, and the basal flow rate 68 (including both a slowly and quickly changing component). The protocols may make use of a model developed from the data collected by the pump 10 from many patients that can help anticipate the effects of pain medication on patient pain and that may be used to guide the reaction of the pump to pain indications by the patient informed by better knowledge of how the pain medication will affect pain going forward. In addition, the protocols may include alarm thresholds (used in process block 58), and the increments of change permitted in each of the dynamic parameters (e.g. dropback time 94, increment of adjustment of basal rate 68, etc.). Generally, the protocols are captured in the logic of the program 40 and in the parameter values used by the program 40 as described.

As noted, the data collected by the pump 10 will be used to refine protocols for operation of the pump 10, however this data may also be used for general recordkeeping and billing purposes. In addition, information collected from the pump 10 may be used to optimize other aspects of the treatment not directly related, to the pump 10 including, for example, catheter placement, timing of catheter placement, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear". "bottom" and "side", describe the orientation or portions of the component within a consistent but arbitrary frame of reference which is made clear by reference to the text and the associated drawings describing the component under discussion. Such terminology may include the words specifically mentioned above, derivatives thereof and words of similar import. Similarly, the terms "first", "second" and other such numerical terms referring to structures do not imply a sequence or order unless clearly indicated by the context. Indication is used herein to mean any type of sense to indication including an audio alarm, visual display or other computer-controlled activation (motor buzz, etc.)

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors or other types of computers, gate arrays or the like that can execute programs and communicate with each other.

Furthermore, references to memory, unless otherwise specified, can include one or more processor-readable and accessible memory elements and/or components that can be internal to the processor-controlled device, external to the processor-controlled device, and can be accessed via a wired or wireless network. The term manual pushbuttons means buttons that may be operated by finger touch or the like including touchscreen and passive switch and mechanical switch.

It will be appreciated that the look-ahead operation of the ambulatory pump 10 described herein is consistent both with anticipatory locking of the pump so that the pump does not exceed the service values, as well as setting the service values to a value below the actual longest desired service value by amount of the typical treatment protocol and allowing the treatment protocol to exceed the service value once, and then locking out pump, in this latter case, the pump lockout anticipates that the next treatment protocol would exceed the remaining operating time or volume (which is a negative value) and need not actually accept a new protocol.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A pump system for managing pain medication comprising:
   a pump for delivery of a pain medication to a patient from a reservoir through a line to a patient;
   an input device having a button actuatable by the patient for receiving a discretionary input from the patient related to patient perception of real time pain during delivery of the pain medication;
   an electronic controller communicating with the pump and the input device executing a stored program contained in non-transitory memory to:
   (a) provide a schedule of pain medication delivery having a basal delivery rate;
   (b) at a first time, control the pump to provide the basal delivery rate of pain medication through the line to the patient;
   (c) at a second time after the first time, receive the discretionary input from the patient through the input device and respond by controlling the pump to:
      (i) deliver a discrete bolus of pain medication through the line only if the discretionary input occurred after a bolus lockout time based on drug adverse effects after any previous delivery of a discrete bolus to the patient and not deliver the discrete bolus of pain medication through the line if the discretionary input occurred before an end of the bolus lockout time, the bolus delivery providing a volume beyond the basal delivery rate;
      (ii) adjust the basal delivery rate upward from the basal rate of the first time only if the discretionary input occurred after an effect lag time different than the bolus lockout time and before the end of the bolus lockout time and do not adjust the basal delivery rate if the discretionary input occurred before an end of the effect lag time, the effect lag time being a time before an effect of the previous delivery of the discrete bolus would be felt, the basal delivery rate being a rate of pain medication delivery outside the bolus delivery.

2. The pump system of claim 1 wherein the discretionary inputs are actuation of the button of the input device.

3. The pump system of claim 1 wherein the discretionary inputs are received through the input device in response to a real-time survey soliciting information about pain from the patient.

4. The pump system of claim 3 wherein the real-time survey provides the patient with a scale of pain levels including descriptions of pain at each level to return a pain quantity.

5. The pump system of claim 1 wherein step (c) further adjusts the bolus volume.

6. The pump system of claim 1 wherein step (c) further adjusts the bolus lockout time.

7. The pump system of claim 1 wherein step (c) responds to a trending of patient discretionary input related to patient perception of real-time pain over a period of time.

8. The pump system of claim 1 wherein the pump system further includes a wireless transceiver and wherein the schedule is received wirelessly from a remote device.

9. The pump system of claim 1 wherein the pump system further includes a wireless transceiver and the input device is a wireless portable device.

10. The pump system of claim 9 wherein the wireless smart device is a cellular telephone providing text entry capability.

11. The pump system of claim 1 wherein the pump records the discretionary inputs from the patient related to patient perception of real-time pain over time to provide a history of patient pain over a time of delivery of the pain medication.

12. The pump system of claim 11 wherein the pump records whether the pump responds to the discretionary input by delivering the discrete bolus or whether the discretionary input is denied delivery of the discrete bolus as being within the bolus lockout time.

13. The pump system of claim 11 wherein the pump system includes a wireless transceiver and operates to communicate the history of patient pain to a remote electronic medical record.

14. The pump system of claim 11 wherein the pump system further records an indication of pain medication delivery over time to provide a history of pain medication delivery over the time of delivery of the pain medication.

15. The pump system of claim 1 wherein the adjustment of the basal delivery rate response to the input from the patient related to real-time pain both operates to increase and to decrease the basal delivery rate.

16. The pump system of claim 1 wherein the input device is a mechanical switch in physical communication with the pump.

17. The pump system of claim 1 wherein the pump system collects pain management information prior, during, and after the delivery of pain medication to provide data for improved pain management.

* * * * *